(12) United States Patent
Bosley et al.

(10) Patent No.: US 7,459,288 B2
(45) Date of Patent: Dec. 2, 2008

(54) METHOD OF PRODUCING RETINYL ESTERS

(75) Inventors: John Anthony Bosley, Kettering (GB); Clive Roderick Harding, Trumbull, CT (US); Christopher Rawlins, Shambrook (GB); Julia Sarah Rogers, Shambrook (GB); Ian Richard Scott, Stratford upon Avon (GB)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 412 days.

(21) Appl. No.: 10/534,520

(22) PCT Filed: Oct. 27, 2003

(86) PCT No.: PCT/EP03/12206

§ 371 (c)(1),
(2), (4) Date: May 11, 2005

(87) PCT Pub. No.: WO2004/044212

PCT Pub. Date: May 27, 2004

(65) Prior Publication Data

US 2006/0183184 A1 Aug. 17, 2006

(30) Foreign Application Priority Data

Nov. 11, 2002 (GB) .................. 0226270.7

(51) Int. Cl.
C12P 13/00 (2006.01)
C12P 7/62 (2006.01)
C12P 7/64 (2006.01)

(52) U.S. Cl. .................... 435/67; 435/134; 435/135
(58) Field of Classification Search .................. None
See application file for complete search history.

(56) References Cited

U.S. PATENT DOCUMENTS 6,479,618 B1 * 11/2002 Vonderhagen .............. 528/274

FOREIGN PATENT DOCUMENTS

| DE | 10018519 | 4/2000 |
|---|---|---|
| EP | 0 094 771 | 5/1983 |
| EP | 0 343 444 | 5/1989 |
| GB | 2 026 319 | 7/1978 |
| JP | 56113760 | 9/1981 |
| JP | 61212515 | 9/1986 |
| JP | 62248495 | 10/1987 |
| JP | 6032774 | 2/1994 |
| WO | 99/32105 | 7/1999 |
| WO | 01/78676 | 10/2001 |

OTHER PUBLICATIONS

International Search Report, PCT/EP03/12206, mailed Mar. 1, 2004, 2 pp.
GB Search Report, GB 0226270.7, dated Apr. 17, 2003, 1 p.
GB Search Report, GB0226270.7, dated May 21, 2003, 1 p.
Maugard, et al., "Enzymatic Synthesis of Derivatives of Vitamin A in Organic Media", Journal of Molecular Catalysis B Enzymatic, vol. 8, No. 4-6, Feb. 18, 2000, pp. 275-280, XP002270197.
O'Connor, et al., "Candida-Cylindracea Lipase-Catalysed Synthesis of Retinyl and Oleyl Palmitates Carbon Chain Length Dependence of Esterase Activity", Australian Journal of Chemistry, vol. 45, No. 4, 1992, pp. 641-649, XP0008027552.
Ajima, et al., "Retinyl Esters Synthesis by Polyethylene Glycol-Modified Lipase in Benzene", Biotechnology Letters, vol. 8, No. 8, 1986, pp. 547-552, XP0008027553.
Dossat, et al., "Lipase-catalysed Transesterification of High Oleic Sunflower Oil", Enzyme and Microbial Technology, vol. 30, No. 1, Jan. 8, 2002, pp. 90-94, XP002270198.
Haraldsson, et al., "The Preparation of Concentrates of Eicosapentaenoic Acid and Docosahexaenoic Acid by Lipase-catalyzed Transesterification of Fish Oil with Ethanol", Journal of the American Oil Chemists' Society, American Oil Chemists' Society Campaign, US, vol. 74, No. 11, Nov. 1, 1997, pp. 1419-1424, XP000736917.

* cited by examiner

*Primary Examiner*—Herbert J Lilling
(74) *Attorney, Agent, or Firm*—Edward A. Squillante, Jr.; Ellen Plotkin

(57) ABSTRACT

A method of producing a retinyl ester compound comprising subjecting a composition comprising retinyl or a retinyl ester and a fat or oil of animal or vegetable origins to enzyme catalysed trans-esterification in solvent free conditions to produce a retinyl ester.

7 Claims, 2 Drawing Sheets

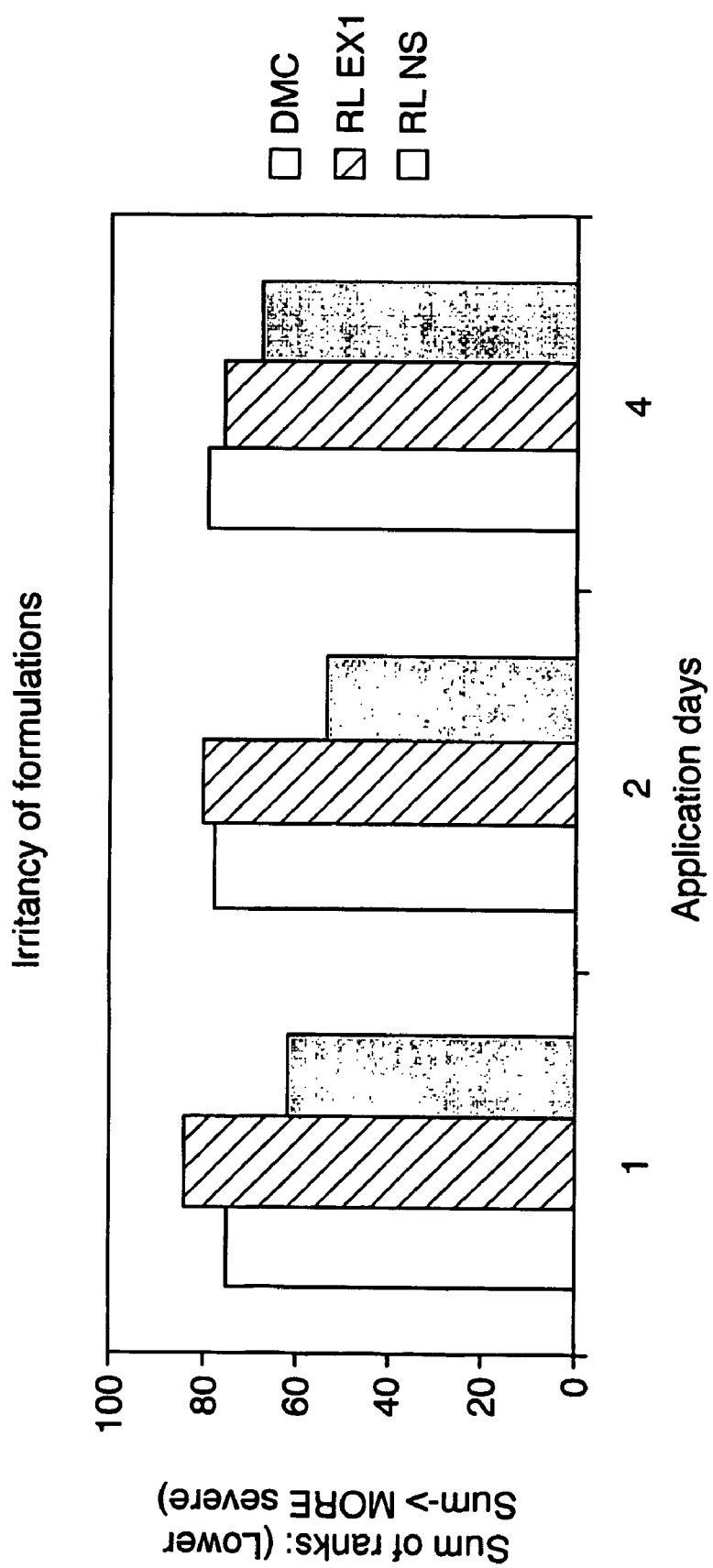

METHOD OF PRODUCING RETINYL ESTERS

This invention relates to a method of producing retinyl esters. In particular, it relates to a beneficial method of producing retinyl esters of fatty acids from natural sources, such as fats and oils of plant and animal origin, using enzyme catalysis. The invention may also provide novel retinyl esters and oil compositions containing retinyl esters, which may be useful adjuncts to cosmetic compositions.

Retinol (vitamin A) and retinyl esters have long been added to cosmetic compositions to provide topical benefits. Retinol may typically be produced on an industrial scale by a totally synthetic route using inter alia acetone. The synthesis may generate retinyl acetate. Retinyl palmitate is another commonly used retinyl ester, which may typically be produced by trans-esterification of retinyl acetate with methyl palmitate, with the reaction being chemically catalysed. Retinyl esters have traditionally been preferred to retinol in topical products since they are easier to formulate, are more stable, and they are less irritant than the alcohol form, with the ester typically being hydrolysed in use to the alcohol on the skin.

It is also known for retinyl esters to be produced using enzymes. For example, JP62248495 describes generally the production of retinyl esters from retinyl acetate and O-methoxypolyethylene glycol modified lipases to produce long chain acid esters. This application also describes the production of retinyl oleate by similarly modified enzymes in a medium comprising benzene saturated with water. However, in this teaching, the reactions between the vitamin A and the long chain fatty acids occur in organic solvent systems, such as e.g. benzene. Also, as the modified lipase is solubilised in the reaction system, significant further processing is required to separate the desired retinyl ester product from the reaction mixture.

It is also known from the Australian Journal of Chemistry, 45 (4) 641-649(1992), O'Connor C. J; Petricevic S. F and Stanley R. A., that C. rugosa can be used in the production of retinyl palmitate from free alcohol and fatty acid in aqueous ethanol or biphasic mixtures of paraffin and water. Again, this process requires the use of organic solvents.

In addition, WO 99/32105 (DCV, Inc) describes the production of conjugated linoleic acid esters in the presence of a lipase, which esters can include retinyl esters. However the application does not state how the retinyl esters were obtained and the examples shown for other esters require the use of solvent and significant processing to isolate the final products.

It is also suggested in Journal of Molecular Catalysis B: Enzymatic, 8, 275-280 (2000) (Maugard T; Legoy M. D) that retinyl esters may be produced by enzymatic routes. The paper describes the production of retinyl adipate, succinate, oleate and lactate for incorporation into cosmetic products. Again the retinyl esters are prepared in solvents using enzymes such as Candida antarctica or Rhizomucor miehei. However, again this document suggests that a solvent is necessary for the reaction to be carried out, and does not discuss the nature or source of the acyl donor.

The present invention aims to provide a new method of preparing retinyl esters for use e.g. in topical cosmetic compositions, which esters may have various benefits associated with them over prior art teachings, including being simpler and cheaper to produce, without the requirement for organic solvents or significant down-stream processing. Surprisingly the products of the invention also show much enhanced stability, and reduced irritancy on the skin.

Thus, according to a first aspect of the invention, there is provided a method of producing a retinyl ester compound comprising subjecting a composition comprising retinol or a retinyl ester and a fat or oil of animal, vegetable or algal origin to enzyme catalysed trans-esterification in solvent free conditions to produce a retinyl ester.

In a further aspect, there is provided a composition comprising a fat or oil of animal, vegetable or algal origin containing retinyl esters of fatty acids contained in the animal, vegetable or algal fat or oil. The retinyl esters are preferably formed by enzyme catalysed trans-esterification.

In yet a further aspect, there is provided a retinyl ester of a fatty acid prepared by the method described above.

According to yet a further aspect there is provided a topical composition for application to human skin containing a retinyl ester or a composition containing a retinyl ester prepared as described above.

According to yet a further aspect there is provided a cosmetic method of treating human skin comprising applying thereto a topical composition as described above.

According to yet a further aspect of the invention, there are provided novel retinyl fatty acid esters, such as (but not necessarily limited to) retinyl C18:3 and C18:4 conjugated fatty acid esters.

The method may be used to provide compositions containing a fat or oil of animal, vegetable or algal origin, and which contain (or from which may be isolated) retinyl esters with fatty acid portions which reflect the fatty acid composition of that animal, vegetable or algal fat or oil. For example, when produced in sunflower oil, the method produces sunflower fatty acid retinyl esters from the enzyme catalysed trans-esterification of sunflower oil. The resultant retinyl esters are predominantly the linoleic and oleic forms, reflecting the fatty acid composition of the sunflower oil.

The method can be extended to the use of any fat or oil of animal, vegetable or algal origin.

As a result, the method can be used to synthesise retinyl esters containing fatty acids having $C_{12-22}$ chain lengths, either saturated or unsaturated. The resulting retinyl esters and retinyl ester blends have been found to be relatively mild compared to e.g. retinyl acetate or retinyl palmitate made by conventional routes. The method also provides a route to the manufacture of retinyl esters and ester blends from a relatively cheap starting material, retinyl acetate, which is cheaper to prepare than materials such as retinyl palmitate.

As an enzyme to be used for the trans-esterfication process, preferably a lipase enzyme is used. Lipase enzymes are well known for their ability to catalyse (trans) esterification reactions involving oils and fats. Any suitable source of lipase can be utilised, though industrially produced lipases are preferred on a cost basis. The lipase should preferably be immobilised on a suitable carrier.

The fat or oil of animal, vegetable or algal origin is in fact a composition which contains either a free fatty acid, or an ester of fatty acids which are of animal, vegetable or algal origin. Any such oil or fat, being of natural origin will typically contain a population of free fatty acids acids or esterified fatty acids, although one or more may predominate in this population. However the population of free fatty acids or esterified fatty acids will typically characterise the animal, vegetable or algal source.

Preferably, a fat or oil of animal, vegetable or algal origin is chosen such that the fatty acid content of the oil or fat of the hydrolysed esters in the oil or fat is relatively enriched in skin benefit agents. Preferred skin benefit agents for the oil or fat may be relatively high in (i.e. contain more than about 0.1%, preferably 0.5%, more preferably more than about 1.0% of) include C18:1-C22:6 fatty acids, particularly petroselinic acid or conjugated 18:2, 18:3 and 18:4 acids.

The invention has a number of benefits and distinguishing features over the prior art.

Firstly, in the process of the invention, retinol is trans-esterified with free fatty acids or more likely (and preferably) fatty acid esters in the oil or fat of animal, vegetable or algal origin. As a result, fatty acid side chains which were previously present in the reaction mixture as a fatty acid side chain in an ester such as a fatty acid triglyceride are now present as part of a retinol ester. Since the retinol ester is hydrolysed on the skin, retinol and the fatty acid are released.

If the fatty acid is also a known skin benefit agent such as e.g. outlined above, on hydrolysis the skin is treated to a "double dose" of skin benefit agents, namely the retinol and the fatty acid, as well as possibly receiving some extra skin benefit from the fat or oil of animal, vegetable or algal origin itself. Fatty acids found in oils or fats of animal, vegetable or algal origin, especially in the triglycerides found therein, may provide a relatively cheap source of such benefit agents. As such, an oil or fat used according to the invention may be selected for its fatty acid profile (either in the form of free fatty acids or triglycerides).

In addition, since the trans-esterification reaction is carried out directly in the fat or oil of animal or vegetable origin in solvent free conditions, which fat or oil may itself have skin beneficial properties, there is no need to conduct any subsequent clean up operation either to remove solvents from the reaction mixture or to isolate or concentrate the retinyl ester. Instead, the fat or oil containing the retinyl ester may be either applied directly to the skin, or dosed into a topical composition for application to the skin. To this end though, it is highly preferred that the enzyme used in the trans-esterification be immobilised on a solid support in such a way that it can be readily removed from the reaction mixture after trans-esterification, for example by filtration.

Such immobilisation techniques are well known in the art, and include for example immobilisation on microporous polypropylene beads which have been pre-treated with surfactant, to which is added an enzyme solution and which is subsequently washed and dried.

The enzyme may be used in normal functional conditions for that enzyme, which typically include simple mixing of the enzyme in a container with the other reactants, at temperatures of up to about 70° C.

As mentioned above the trans-esterification reaction is carried out in solvent free conditions. By this is meant that the composition contains less than about 10% solvent, preferably less than about 5% solvent, more preferably less than about 1% solvent, and preferably is totally solvent free.

Solvents which are excluded from the transesterification reaction include water (the only water present is preferably only that which is associated with the enzyme itself), as well as short chain (i.e $C_{1-6}$) solvents such as alkanes and alcohols, ketones and any esters which may interfere with the desired trans-esterification reaction.

The tranesterification reaction should take place in a medium which has a significant liquid phase, e.g. is a liquid or a paste.

Many preferred fatty acids which are the subject of the trans-esterification reaction are liquid at room temperature; many also contain a degree of unsaturation.

Retinyl esters produced according to the invention which have a fatty acid profile based on the fatty acid content of the corresponding animal, vegetable or algal oil or fat have been found to have surprisingly good physical stability compared to other single species fatty acid esters, as well as be surprisingly mild.

The resultant transesterified esters reflect the fatty acid chain length composition of the animal or vegetable oil used in the method. Hence exemplary retinyl esters which may be prepared according to the invention are prepared using the following plant and animal oils, and may have enriched fatty acid ester contents as outlined below:

C12:0—coconut oil, palm kernal
C14:0 and C14:1—kombo nut (Pycnanthus angolensis) oil
C16:0—palm oil
C18:0 and C18:1—cocoa butter
C18:1—high oleic sunflower oil, olive oil, coriander seed oil
C18:1 and C18:2—corn oil, sunflower oil, cotton seed oil
C18:2—safflower oil, grape seed oil, wheatgerm oil
C18:3—borage oil, evening primrose oil, linseed oil, pine nut oils, Manketti nut oiland pomegranate seed oil
C18:4—*Impatiens balsamina* seed oil
C20:5 and C22:6—fish oils, algal oils
C22:1—crambe oil, mustard seed oil Preferred retinyl esters include those prepared from the fatty acids of plant oils, especially kombo nut oil, coriander oil, sunflower oil, safflower oil, pomegranate oil, borage oil and pine nut oil, as well as retinyl esters of conjugated fatty acids, especially C18 conjugated fatty acids. Unless otherwise purified the retinol esters which are the subject of the invention will invariably comprise a range of fatty chain lengths and types which reflect the fatty acid content of the fat or oil of animal or vegetable origin, or more likely its triglyceride fatty acid content.

Preferred species of retinyl conjugated fatty acid esters which are believed to be novel in their own right include:

retinyl ester of punicic acid (18:3, c9, t11, c13), which can be prepared from pomegranate seed oil retinyl ester of calendic acid (18:3, t8, t10, c12), which can be prepared from *Calendula officinalis* (Marigold) seed oil.

retinyl ester of eleostearic acid (18:3, c9, t11, t13), which can be prepared from Manketti nuts (*Ricinodendron rautanenii* or *Ricinodendron heudelotti*), but which can also be prepared from cherry kernal oils (*Prunus Cerasus, P. avium, P. mahaleb*), tung oil, *Momordica dioica* (Chinese bitter melon), *Parinari montana* and *Parinarium excelsis*.

retinyl ester of parinaric acid (18:4, c9, t11, t13, c15), which is preferably sourced from *Impatiens balsamina* L, but may also be sourced from *Parinari glaberrimum, Lithospermum euchromum, Sebastiana brasiliensis, I. Edgeworthii, I. Pallida & capensis* and *Parinarium laurinum*.

The enzyme used in the method according to the invention is preferably a lipase enzyme, more preferably a lipase immobilised on a solid support. Examples of suitable lipase enzymes include *Candida rugosa* lipase, Lipase D and Lipozyme IM. Methods of immobilisation of lipases (where required) are described, for example, in EP424130.

Topical compositions for application to the human skin preferably comprise 0.00001 to 5%, preferably 0.0001 to 1%, more preferably 0.01 to 0.5% of the retinyl esters prepared according to the invention.

The invention will now be prepared by way of example only with reference to the accompanying drawings, in which:

FIG. 3 shows the relative irritancy of retinyl ester formulations.

EXAMPLE 1

Figure 1:
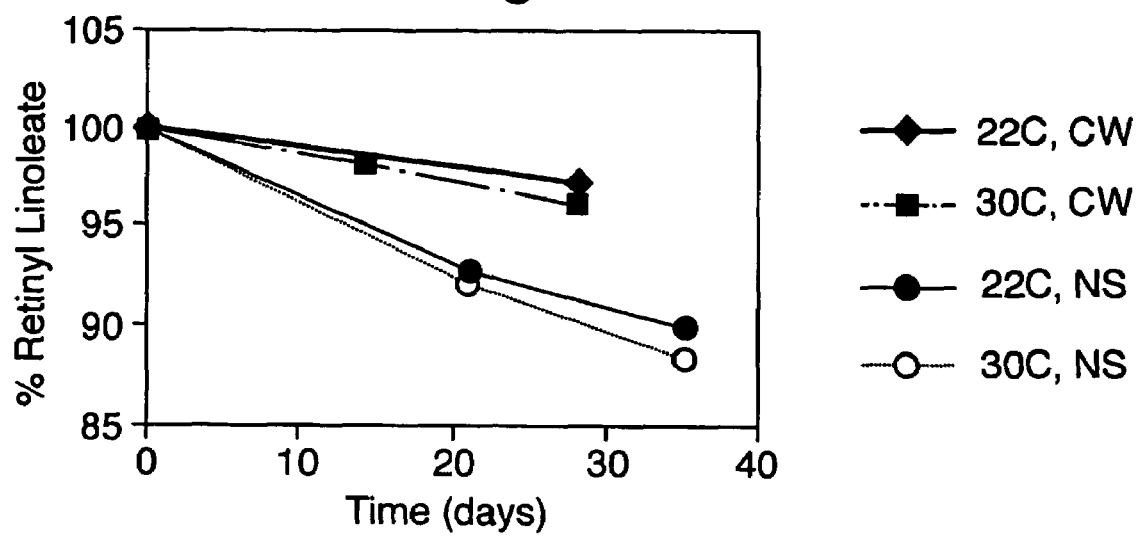
FIG. 1 shows the stability of retinyl esters according to the invention compared to commercially available retinyl palmitate and retinyl linoleate.

Production of Retinyl Esters Using Sunflower Oil

Sunflower oil (7.5 g) and retinyl palmitate (2.5 g) were mixed and water (0.03 g) and immobilised Lipase D (Rhizopus oryzae (Amano) immobilised on Accurel® EP100 macroporous polypropylene (Acordis) 0.1 g) or Candida rugosa AY (Amano) on Accurel® EP100 (Acordis) (CR; 0.1 g)

added. The mixtures were placed in a shaking water bath at 55° C. for 20 or 23 hours. The immobilised lipase was then removed by simple filtration to directly yield the product, a solution of retinol esters in triglyceride oil. The composition of the retinyl esters was separated from the triglycerides by thin layer chromatography (0.5 mm silica G plates, Analtech Ltd.) using toluene as eluting solvent and visualised by spraying with 1% 2,7-dichlorofluorescein in ethanol. The ester band was scraped off and FAMEs were produced using 3 ML sodium methoxide and 1 mL toluene at 80° C. for 20 minutes followed by 5 minutes at 80° C. with boron trifluoride (2 mL volumes of reagent). The fatty acid content was then analysed by Fatty acid methyl ester Gas Chromatography (FAME-GC). GC conditions: Column—30 m/0.53 mm/0.5 um restek famewax, Helium carrier gas 15 kpa, flame ionisation detection, 260° C. PTV injection (Run: 3 min @ 260° C., 80° C. hold 1 min, +20/min to 180° C., +2/min to 220° C., +1/min to 230° C., +4 min hold at 230° C.).

As shown in Table 1, the palmitic acid content of the retinyl ester was reduced from 98.5%, being replaced predominantly by linoleic and oleic acids. The palmitic acid was incorporated into the sunflower triglycerides

TABLE 1

Sunflower retinyl esters produced from retinyl palmitate

| Sample | C14:0 | C16:0 | C18:0 | Other | C18:1 (oleate) | C18:2 (linoleate) | C18 (tot) |
|---|---|---|---|---|---|---|---|
| Retinyl palmitate starting material | 0.4 | 98.5 | 0.7 | 0.4 | 0 | 0 | 0.7 |
| Retinyl ester product (CR - 23 h) | 0.2 | 44 | 5.1 | 0.4 | 16.9 | 33.4 | 55.4 |
| Retinyl ester Product (LD - 20 h) | 0.2 | 28.9 | 5.1 | 1.7 | 21.2 | 42.9 | 69.2 |

EXAMPLE 2

Production of Sunflower Oil Retinyl Esters from Retinyl Acetate

Sunflower oil (7.5 g) and retinyl acetate (3.75 or 2.5 g) were mixed and water (0.03 g) and 1% immobilised Rhizomucor miehei lipase (Lipozyme IM Novo Nordisk) added. The mixture was placed in a shaking water bath at 55° C. for 4 days. The immobilised lipase was then removed by simple filtration to directly yield the product, a solution of retinol esters in triglyceride oil. The levels of retinyl esters were determined by peak collection from HPLC, with the addition of C17 methyl ester ISTD according to the following conditions:

Column: 10 cm Nucleosil 100A 3 um silica with precolumn.

Elution solvents—Solvent A—hexane/toluene 1:1; Solvent B—toluene/ethyl acetate/formic acid 600/200/16; solvent C—toluene/ethyl acetate/isopropyl alcohol/formic acid 500/200/100/16.

| Time (Mins) | Solvent ratios (A/B/C) |
|---|---|
| 0 | 99/1/0 |
| 4.9 | 99/1/0 |
| 5 | 90/10/0 |
| 6 | 75/25/0 |
| 7 | 40/60/0 |
| 9 | 10/90/0 |
| 9.1 | 0/10/90 |
| 12 | 0/10/90 |
| 12.1 | 10/90/0 |
| 15.0 | 10/90/0 |
| 15.1 | 99/1/0 |
| 30.0 | 99/1/0 |

Flow rate: 1.4 mL/min

Detection: Evaporative light scattering detector (40° C./10 L/min nitrogen)

The retinyl ester levels produced are shown in Table 2. The retinyl esters collected from the HPLC were converted to FAMEs using 2 ML sodium methoxide at 80° C. for 20 minutes. FAME-GC was performed as described previously (Table 3).

TABLE 2

Retinyl ester levels

| Description | % Long chain retinyl esters |
|---|---|
| 2:1 SF:RA Lipase SP392(supported) 4 days | 20.4 |
| 3:1 SF:RA Lipase SP392(supported) 4 days | 17.3 |

TABLE 3

Fatty acid profile of retinyl esters

| Fatty acid chain length | 2:1 SF:RA | 3:1 SF:RA |
|---|---|---|
| 16:0 | 14.2 | 12.7 |
| 16:1 | 0.9 | 3.4 |
| 18:0 | 5.1 | 5.0 |
| 18:1 | 22.6 | 22.2 |
| 18:2 | 55.1 | 54.3 |
| 18:3 | 0 | 0.3 |
| 20:0 | 0.8 | 0.7 |
| 20:1 | 0.8 | 0.1 |

TABLE 3-continued

Fatty acid profile of retinyl esters

| Fatty acid chain length | 2:1 SF:RA | 3:1 SF:RA |
|---|---|---|
| 22:0 | 0.5 | 0.9 |
| 22:1 | 0 | 0.4 |

EXAMPLE 3

Retinyl Linoleate Stability in Moisturising Cream Formulations

Figure 2:
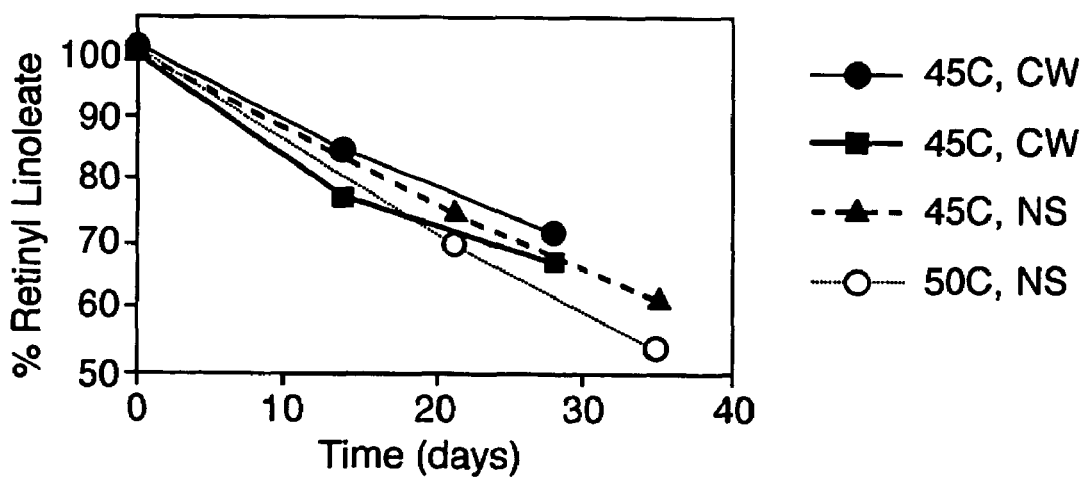
FIG. 2 shows the comparative stability of esters according to the invention in topical products.

Retinyl Linoleate from National Starch Corp. and the retinyl ester product from example 1 were blended into moisturising cream formulations shown below in Formulations 1 and 2 at a level of 0.03 and 0.15% of the retinyl ester. The creams were stored at 22° C., 30° C., 45° C. and 50° C. and samples taken at time 0, and twice more over 35 days as shown in FIGS. 1 and 2.

Formulation 1

| Ingredient Name | % | Supplier |
|---|---|---|
| Phase A | | |
| Water | to 100 | Local |
| Water, Spring | 1.00 | Local, Poland Springs |
| Glycerin | 5.00 | Dow |
| Disodium EDTA | 0.05 | W R. Grace |
| Panthenol | 0.10 | Roche |
| Mg Amino Acid Chelate | 0.01 | Maypro |
| Zn Amino acid Chelate | 0.01 | Maypro |
| Green Tea extract | 0.10 | Tri-K |
| Grapeseed Extract | 0.10 | Brooks |
| Phase B | | |
| Ultrez 10 | 0.75 | B F Goodrich |
| TEA 99% | 2.00 | Dow |
| Parsol HS | 2.00 | Roche |
| Water | 10.00 | Local |
| Lanett 14 (Myristal Alcohol) | 0.50 | Cognis |
| Arlacel 60 (Sorbitan Stearate) | 1.20 | ICI |
| Cetyl Alcohol | 0.50 | Hankel |
| Emulsynt GDL (Glycerol Dilaurate) | 0.50 | ISP |
| Stearyl Alcohol | 0.50 | RTD |
| Ryoto Sugar Ester | 0.25 | Ryoto |
| Myrj 59 (PEG-100 Stearate) | 0.50 | ICI |
| Pristerene 4911 (Stearic Acid) | 0.25 | Stephan |
| Parsol MCX (Octyl methoxy cinnimate) | 4.322 | Roche |
| Parsol 1789 (Butyl Methoxy dibenzoyl . . . ) | 2.00 | Roche |
| Dermablock OS (Octyl Salicylate) | 3.90 | Alzo |
| Vitamin E Acetate | 0.10 | Roche |
| Retinyl linoleate-National Starch | 1.5 | |
| Incromide LSM Linoleate | 0.01 | Croda |
| Cholesterol NF | 0.10 | Croda |
| BHT | 0.02 | |
| Tocomix | 0.003 | |
| Permethyl 101A | 4.50 | Presperse |
| Phenonip | 0.54 | Clariant |

| Ingredient Name | % | Supplier |
|---|---|---|
| Phase C | | |
| Vitamin A Palmitate | 0.01 | Roche |
| Fragrance Q26913 | 0.20 | Quest |
| TOTAL | 100.00 | |

Formulation 2

| Ingredient Name | % | Supplier |
|---|---|---|
| Water | to 100 | Local |
| Water, Spring | 1.00 | Local, Poland Springs |
| Glycerin | 5.00 | Dow |
| Disodium EDTA | 0.05 | W R Grace |
| Panthenol | 0.10 | Roche |
| Mg Amino acid Chelate | 0.010 | Maypro |
| Zn Amino acid chelate | 0.010 | Maypro |
| Green Tea Extract | 0.100 | Tri-K |
| Grape seed extract | 0.100 | Brooks |
| Phase B | | |
| Ultrez 10 | 0.75 | B F Goodrich |
| TEA 99% | 2.00 | Dow |
| Parsol HS | 2.00 | Roche |
| Water | 10.00 | Local |
| Lanett 14 (Myristal Alcohol) | 0.50 | Cognis |
| Arlacel 60 (Sorbitan Stearate) | 1.20 | ICI |
| Cetyl Alcohol | 0.50 | Hankel |
| Emulsynt GDL (Glycerol Dilaurate) | 0.50 | ISP |
| Stearyl Alcohol | 0.50 | RTD |
| Ryoto Sugar Ester | 0.25 | Ryoto |
| Myrj 59 (PEG-100 Stearate) | 0.50 | ICI |
| Pristerene 4911 (Stearic Acid) | 0.25 | Stephan |
| Parsol MCX (Octyl methoxy Cinnimate . . . ) | 4.577 | Roche |
| Parsol 1789 (Butyl Methoxy dibenzoyl . . . ) | 2.00 | Roche |
| Dermablock OS (Octyl Salicylate) | 3.12 | Alzo |
| Retinyl linoleate (from example 1) | 1.5 | |
| Incromide LSM (Linoleamide MEA) | 0.01 | Croda |
| Cholesterol NF | 0.10 | Croda |
| BHT | 0.02 | |
| Tocomix | 0.003 | |
| Permethyl 101A | 4.50 | Presperse |
| Phenonip | 0.54 | Clariant |
| Phase C | | |
| Fragrance Q26913 | 0.20 | Quest |
| Vitamin A Palmitate | 0.01 | Roche |
| TOTAL | 100.00 | |

The retinyl esters were extracted from the base cream 60/40 acetone/acetonitrile, stirred for 10 minutes, filtered and then injected These were then analysed by HPLC according to the conditions below.

Column: Intersil 5 micron, ODS-2 (C18) from Phenominex

Detection: UV at 325 nm

Mobile phase: 35% Acetone/65% Acetonitrile

Flow Rate: 1.0 mL/minute

Peak Elution: Approx 10 minutes

Calib Curve: Standards—1.5 ppm to 18 ppm for samples containing 0.03 to 0.15% RL.

FIGS. 1 and 2 show the stability results for the samples. The retinyl ester product from example 1 was more stable than the National Starch originating retinyl linoleate. For comparison retinyl palmitate is only as stable as retinyl linoleate (National Starch).

EXAMPLE 4

Stability of Retinyl Esters in Oils

The stability of retinyl linoleate (National Starch) and retinyl esters (example 1) in the fluid oil phase alone of a moisturising cream formulation as evaluated. Two fluid oil formulations were prepared by incorporating the desired amounts of the ingredients like Parsol MCX, Dermablock OS, Permethyl 101A and Vitamin E acetate as found in Formulation 1. One was spiked with retinyl esters (example 1) and the other with retinyl linoleate from National Starch (NS) at the 0.75% level. These were analysed initially and after twenty eight days at 50° C. (Table 4)

TABLE 4

Stability of retinyl esters in the oil phase

| Retinyl esters | % recovery |
|---|---|
| Retinyl linoleate (NS) | 72.6 |
| Retinyl esters (Example 1) | 85.0 |

The data demonstrates that retinyl esters from example 1 are more stable in oil blends than retinyl linoleate.

EXAMPLE 5

Irritancy of Retinyl Esters 5 male and 15 female subjects were selected for the study, the aim of which was to compare the irritation potential of a moisturising cream alone and in combination with retinyl linoleate from example 1 vis National Starch material. The concentration of retinyl linoleate added to the moisturising cream from the 2 sources contained equal molar quantities of the retinyl moiety in ester form. Test materials were compared to a selected control statistically in a pairwise comparison based on Friedman's Rank Sums (p<0.10 is considered significant, p values 0.2 and 0.15 are provided for informational purposes only).

Protocol

The upper outer aspect of the upper arm was exposed to the test materials once for a 24 hour period followed by up to three 18 hour exposures, using 25 mm Hill Top® Chambers fitted with 18 mm Webril® padding and held in place with Scanpor® tape. 0.2 ml of the test materials was applied to the Webril® padding 1 hour before application.

Dose Characterization/Verification and Stability and Microbiology:

The level of Retinyl linoleate was within target for all Test materials containing this material. All Test materials were found to be microbiology acceptable.

As shown in FIG. 3, the retinyl linoleate from example 1 (RL EX1) is far less irritant than the retinyl linoleate from National starch (RL NS).

EXAMPLE 6

Production of Retinyl Esters from Naturals Oils and Retinyl Acetate

Retinyl esters were prepared using natural oils including Sunflower oil, coriander oil and hexane extracts of pomegranate, *Impatiens balsimina,* and Manketti seeds. The oils and retinyl acetate were mixed in a ratio 3:1 (7.5 g:2.5 g) with water (0.03 g) and either 1% immobilised *Rhizomucor miehei* lipase (Lipozyme IM Novo Nordisk) or Lipase D. The mixture was placed in a shaking water bath or stirred vessel at 55° C. for 4 days. The immobilised lipase was then removed by simple filtration to directly yield the product, a solution of retinol esters in triglyceride oil. The retinyl esters were analysed using solid phase extraction (SPE) column separation followed by gas chromatography (GC) as described below.

Analysis method: 20 mgs of retinyl ester/oil along with a methyl ester internal standard were dissolved in 0.5 mL hexane and loaded onto a 0.5 g silica SPE column. Retinyl esters and the methyl ester internal standard were eluted with 10 mL 2% diethyl ether in hexane. Retinyl esters were converted to methyl esters and the fatty acid composition quantified against by GC.

TABLE 4

Analysis of retinyl esters

| Fatty acid chain length | Coriander esters | Pomegranate esters | Manketti esters | Impatiens esters |
|---|---|---|---|---|
| 16:0 | 26.3 | 27.0 | 42.9 | 35.5 |
| 18:0 | 1.8 | 2.6 | 5.4 | 4.9 |
| 18:1 | 59.6 Petroselinic | 4.4 | 4.3 | 9.6 |
| 18:2 | 8.4 | 3.9 | 8.9 | 6.3 |
| 18:3 | | 52.3 Punicic | 32.4 Eleostearic | 11.3 |
| 18:4 | | | | 16.3 Parinaric |
| C18 total | 69.8 | 68.5 | 51.3 | 51.5 |
| other | 3.9 | 9.8 | 6.1 | 16.1 |

The invention claimed is:

1. A method of producing a retinyl ester compound comprising subjecting a composition comprising retinol or a retinyl ester and a fat or oil of animal or vegetable origins to enzyme catalysed transesterification in solvent free conditions to produce a retinyl ester.

2. A method according to claim 1 wherein the fat or oil of animal or vegetable origin contains one or more $C_{12-22}$ saturated or unsaturated fatty acids.

3. A method according to claim 1 wherein the enzyme is a lipase enzyme.

4. A method according to claim 1 wherein the enzyme is immobilised on a support.

5. A method according to claim 1 wherein the fat or oil of animal or vegetable origin contains a fatty acid triglyceride.

6. A method according to claim 1 wherein the source of the fatty acid is kombo nut oil, coriander oil, sunflower oil, safflower oil, pomegranate seed oil, Manketti nut oil, fish oil, borage oil, pine nut oil or *Impatiens balsamina* seed oil or *calendula* seed oil.

7. A method according to claim 1 wherein the enzyme is immobilised on a solid support.

* * * * *